(12) United States Patent
Ahmad et al.

(10) Patent No.: US 9,987,445 B2
(45) Date of Patent: Jun. 5, 2018

(54) CONTINUOUS POSITIVE AIRWAY PRESSURE THERAPY TARGET PRESSURE COMFORT SIGNATURE

(71) Applicant: BREATHE TECHNOLOGIES, INC., Irvine, CA (US)

(72) Inventors: Samir S. Ahmad, San Diego, CA (US); Dongbing Wei, Rancho Santa Margarita, CA (US); Mark Peilemeier, Irvine, CA (US); Leonardo Alberto Baloa-Welzien, Lake Forest, CA (US)

(73) Assignee: Breathe Technologies, Inc., Irvine, CA (US)

( * ) Notice: Subject to any disclaimer, the term of this patent is extended or adjusted under 35 U.S.C. 154(b) by 550 days.

(21) Appl. No.: 14/482,444

(22) Filed: Sep. 10, 2014

(65) Prior Publication Data
US 2015/0068528 A1     Mar. 12, 2015

Related U.S. Application Data

(60) Provisional application No. 61/876,135, filed on Sep. 10, 2013.

(51) Int. Cl.
*A61M 16/00* (2006.01)
*A61M 16/06* (2006.01)
*A61M 16/10* (2006.01)

(52) U.S. Cl.
CPC .... *A61M 16/0069* (2014.02); *A61M 16/0051* (2013.01); *A61M 16/026* (2017.08);
(Continued)

(58) Field of Classification Search
CPC .............. A61M 16/00; A61M 16/0003; A61M 16/0057; A61M 16/0066; A61M 16/06; A61M 16/202; A61M 16/204; A61M 16/205; A61M 16/0051; A61M 16/0069; A61M 16/021; A61M 16/022; A61M 16/024; A61M 2205/50; A61M 2205/502; A61M 2205/52

See application file for complete search history.

(56) References Cited

U.S. PATENT DOCUMENTS 5,134,995 A * 8/1992 Gruenke ............... A61M 16/00
                                                    128/204.21
5,535,738 A    7/1996 Estes et al.
(Continued)

FOREIGN PATENT DOCUMENTS

FR        2694697 A1    2/1994
WO   2013130645 A1    9/2013

OTHER PUBLICATIONS

International Search Report and Written Opinion for PCT/US14/55022 (7 pages), dated Dec. 17, 2014.
European Search Report for EP 14 84 4253; dated Apr. 5, 2017.

*Primary Examiner* — (Jackie) Tan-Uyen T Ho
*Assistant Examiner* — Joseph D Boecker
(74) *Attorney, Agent, or Firm* — Stetina Brunda Garred & Brucker (57) ABSTRACT

A comfort signature that naturally adapts delivered pressure to patient breathing by measuring comfort directly from the source is disclosed. Pressure is measured at the patient interface and is used to provide a comfortable and suitable target pressure adjustment that is synchronized with patient respiration.

17 Claims, 4 Drawing Sheets

(52) U.S. Cl.
CPC .......... *A61M 16/06* (2013.01); *A61M 16/107* (2014.02); *A61M 2016/0021* (2013.01); *A61M 2016/0027* (2013.01); *A61M 2205/18* (2013.01); *A61M 2205/3365* (2013.01); *A61M 2205/42* (2013.01); *A61M 2205/505* (2013.01)

(56) References Cited

U.S. PATENT DOCUMENTS

| | | | | |
|---|---|---|---|---|
| 5,540,220 | A * | 7/1996 | Gropper | A61M 16/024 128/204.21 |
| 5,865,173 | A * | 2/1999 | Froehlich | A61M 16/024 128/204.21 |
| 6,629,527 | B1 * | 10/2003 | Estes | A61M 16/024 128/202.22 |
| 6,932,084 | B2 | 8/2005 | Estes et al. | |
| 6,948,497 | B2 | 9/2005 | Zdrojkowski et al. | |
| 7,100,607 | B2 | 9/2006 | Zdrojkowski et al. | |
| 7,942,824 | B1 * | 5/2011 | Kayyali | A61B 5/021 128/204.23 |
| 8,899,231 | B2 * | 12/2014 | Bassin | A61M 16/00 128/204.21 |
| 2002/0007127 | A1 * | 1/2002 | Sullivan | A61B 5/097 600/529 |
| 2003/0111079 | A1 * | 6/2003 | Matthews | A61M 16/0051 128/204.18 |
| 2003/0192544 | A1 * | 10/2003 | Berthon-Jones | A61M 16/024 128/204.18 |
| 2004/0016433 | A1 * | 1/2004 | Estes | A61M 16/024 128/204.21 |
| 2005/0005937 | A1 * | 1/2005 | Farrugia | A61B 5/08 128/204.18 |
| 2005/0268913 | A1 * | 12/2005 | Morris | A61M 16/00 128/204.23 |
| 2006/0037615 | A1 * | 2/2006 | Wilkinson | A61B 5/08 128/204.23 |
| 2006/0130835 | A1 * | 6/2006 | Truschel | A61M 16/12 128/204.21 |
| 2006/0150974 | A1 * | 7/2006 | Berthon-Jones | A61B 5/085 128/204.21 |
| 2006/0211950 | A1 * | 9/2006 | Brunner | A61B 5/085 600/538 |
| 2006/0249149 | A1 * | 11/2006 | Meier | A61B 5/087 128/204.18 |
| 2007/0017518 | A1 | 1/2007 | Farrugia et al. | |
| 2007/0215156 | A1 * | 9/2007 | Kwok | A61F 5/56 128/204.21 |
| 2008/0053444 | A1 | 3/2008 | Estes et al. | |
| 2008/0251079 | A1 * | 10/2008 | Richey | A61M 16/0051 128/204.26 |
| 2009/0020121 | A1 | 1/2009 | Bassin | |
| 2009/0050154 | A1 * | 2/2009 | Strothmann | A61M 16/0051 128/204.23 |
| 2009/0095297 | A1 * | 4/2009 | Hallett | A61M 16/0051 128/204.18 |
| 2009/0188502 | A1 * | 7/2009 | Tiedje | A61M 16/0051 128/204.23 |
| 2009/0301488 | A1 * | 12/2009 | Sun | A61M 16/0051 128/204.23 |
| 2011/0284003 | A1 | 11/2011 | Douglas et al. | |
| 2012/0024286 | A1 * | 2/2012 | Boring | A61M 16/0051 128/204.21 |
| 2012/0065533 | A1 | 3/2012 | Carrillo, Jr. | |
| 2012/0227740 | A1 | 9/2012 | Berthon-Jones et al. | |
| 2012/0291785 | A1 * | 11/2012 | Ramanan | A61M 16/0051 128/204.23 |
| 2013/0206144 | A1 * | 8/2013 | Ahmad | A61M 16/00 128/204.23 |
| 2013/0255687 | A1 * | 10/2013 | Rahlf | A61M 16/00 128/204.26 |
| 2015/0265789 | A1 * | 9/2015 | Whiting | A61B 5/04 128/204.23 |

* cited by examiner

CONTINUOUS POSITIVE AIRWAY PRESSURE THERAPY TARGET PRESSURE COMFORT SIGNATURE

CROSS-REFERENCE TO RELATED APPLICATIONS

This application relates to and claims the benefit of U.S. Provisional Application No. 61/876,135 filed Sep. 10, 2013 and entitled "CONTINUOUS POSITIVE AIRWAY PRESSURE THERAPY TARGET PRESSURE COMFORT SIGNATURE", the entire disclosure of which is hereby wholly incorporated by reference.

STATEMENT RE: FEDERALLY SPONSORED RESEARCH/DEVELOPMENT

Not Applicable

BACKGROUND OF THE INVENTION

1. Technical Field

The present disclosure relates generally to the treatment of respiratory conditions with the delivery of pressurized flow of breathable gas to a patient and more particularly, to a continuous positive airway pressure (CPAP) target pressure comfort signature that naturally adapts blower pressure to patient breathing by measuring comfort directly from the source, e.g., measuring pressure at the patient airway.

2. Related Art

Sleep apnea is a serious medical condition in which patient breathing during sleep pauses abnormally, or is abnormally low. Apnea is categorized as obstructive, central, and combined obstructive and central, though the obstructive sleep apnea (OSA) is the most common. The patient's upper airway repeatedly narrows or collapses, causing pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles resulting from patients gasping for air. There have been studies linking sleep apnea to more severe long-term health issues including heart disease and depression, and recently, to cancer as well. With apnea being strongly linked to obesity, and with obesity being projected to increase, the number of patients suffering from sleep apnea is likely to increase concomitantly.

One common treatment for obstructive sleep apnea is continuous positive airway pressure (CPAP) therapy, where a positive pressure is applied to the patient to prevent its collapse as would otherwise occur during an apnea episode. By retaining the patient's airway, normal, uninterrupted breathing during sleep is ensured. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. Earlier patient breathing assistance devices tended to be uncomfortable to use because of the bulkiness associated with the patient interface, as well as the misapplication of pressure resulting from sub-optimal control methodologies. Various improvements have been developed to reduce discomfort during therapy, particularly at critical points along the patient's respiratory cycle. Thus, what was previously prescribed only for the more severe cases of sleep apnea in which the benefits of treatment outweighed the significant discomfort is now useful for treating a wider spectrum of sleep apnea conditions.

Adherence to CPAP therapy is difficult for some patients with obstructive sleep apnea and especially for those who have difficulty exhaling against a constant pressure at the mask that they need to wear at night while sleeping or attempting to sleep. Many patients describe the experienced sensation as being akin to asphyxiating. Furthermore, to maintain airway patency and thus treat OSA, positive pressure is only needed during the end of exhalation to the beginning of inhalation, at which time this positive pressure acts a pneumatic splint to hold the upper airway open. Based on this finding, several technological advancements have been developed including bi-level pressure and pressure relief.

In bi-level CPAP therapy, two pressures are used during patient's breathing cycle: a high pressure during inspiration, normally called inspiratory positive airway pressure (IPAP), and another lower pressure during exhalation, normally called exhaled positive airway pressure (EPAP). One advantage of this technique is that the patient feels the device is synchronized to their breathing, which elevates their degree of comfort. However, bi-level CPAP therapy suffers from a major disadvantage, namely, that in order to implement the feature in hardware more costly components than a regular CPAP system are required. Cost issues are a serious concern in the development and marketing of CPAP systems, as they are intended for purchase by the end-user patient.

A more recent and less costly solution to relieving pressure during exhalation to improve patient comfort is the development of pressure relief technology. The broad concept is to detect inspiration and exhalation phases of the breathing cycle, and at the time of exhalation, relieve pressure momentarily either in accordance with the shape of the patient's airflow rate and/or disengaging power to the blower at the beginning of inhalation. Both of these techniques rely on a flow signal to determine the timing of pressure relief. However, the use of a flow signal suffers from various deficiencies as well, and as such may not achieve the highest possible degree of comfort.

Existing systems are generally limited to guessing what comfort is needed based on flow signal, and provide "relief" accordingly. Accordingly, there is a need in the art for a CPAP target pressure comfort signature that naturally adapts blower pressure to patient breathing by measuring comfort directly from the source.

BRIEF SUMMARY OF THE INVENTION

The present disclosure is directed to a CPAP comfort signature based upon measurements of pressure at the patient so that a more comfortable and suitable pressure can be provided with better synchrony with the patient's spontaneous breathing efforts.

One embodiment of the disclosure is directed to a method for adjusting CPAP therapy for patient comfort on a respiratory assistance device. The method may begin with setting a target delivery pressure to a prescription pressure level. Thereafter, the method may include generating an output of therapeutic gas to an airway of the patient. The output may be generated on the respiratory assistance device, and further, the airway of the patient may be in pneumatic communication with the respiratory assistance device over a patient interface. The pressure of the output may correspond to the target delivery pressure as set to the prescription pressure level. The method may further include receiving patient pressure values measured at the patient interface. These values may be received on the respiratory assistance device. There may also be a step of detecting a minimum value among the received patient pressure values over a first predetermined time period. Furthermore, the method may include reducing the target delivery pressure following a predefined delay after detecting the minimum value of the received patient pressure values. This reduction in target delivery pressure may continue until the target delivery it is below a contemporaneously measured patient pressure value.

According to another embodiment of the disclosure, a method for adjusting target delivery pressure to a patient undergoing continuous positive airway pressure therapy is contemplated. The method may include detecting a minimum value of patient pressure corresponding to a time of onset of patient expiration. There may also be a step of reducing target pressure following a variable time after the detecting of the minimum value of patient pressure. This reducing step may continue until actual delivered pressure is evaluated as being at least below the target pressure. The method may also include increasing the target pressure after the actual delivered pressure is evaluated as being at least below the target pressure.

Another embodiment of the present disclosure may be directed to an article of manufacture comprising a program storage medium. Such medium may be readable by a data processing apparatus and may tangibly embody one or more programs of instructions executable by the data processing apparatus to perform the aforementioned method for adjusting continuous positive airway pressure therapy for patient comfort, as well as the aforementioned method for adjusting target delivery pressure to a patient undergoing continuous positive airway pressure therapy.

The present invention is best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and detailed description to indicate like elements.

DETAILED DESCRIPTION OF THE INVENTION

The detailed description set forth below in connection with the appended drawings is intended as a description of the presently preferred embodiment of continuous positive airway pressure (CPAP) target comfort signatures, and is not intended to represent the only form in which the presented embodiments may be developed or utilized. It is further understood that the use of relational terms such as first and second and the like are used solely to distinguish one from another entity without necessarily requiring or implying any actual such relationship or order between such entities.

Figure 1:
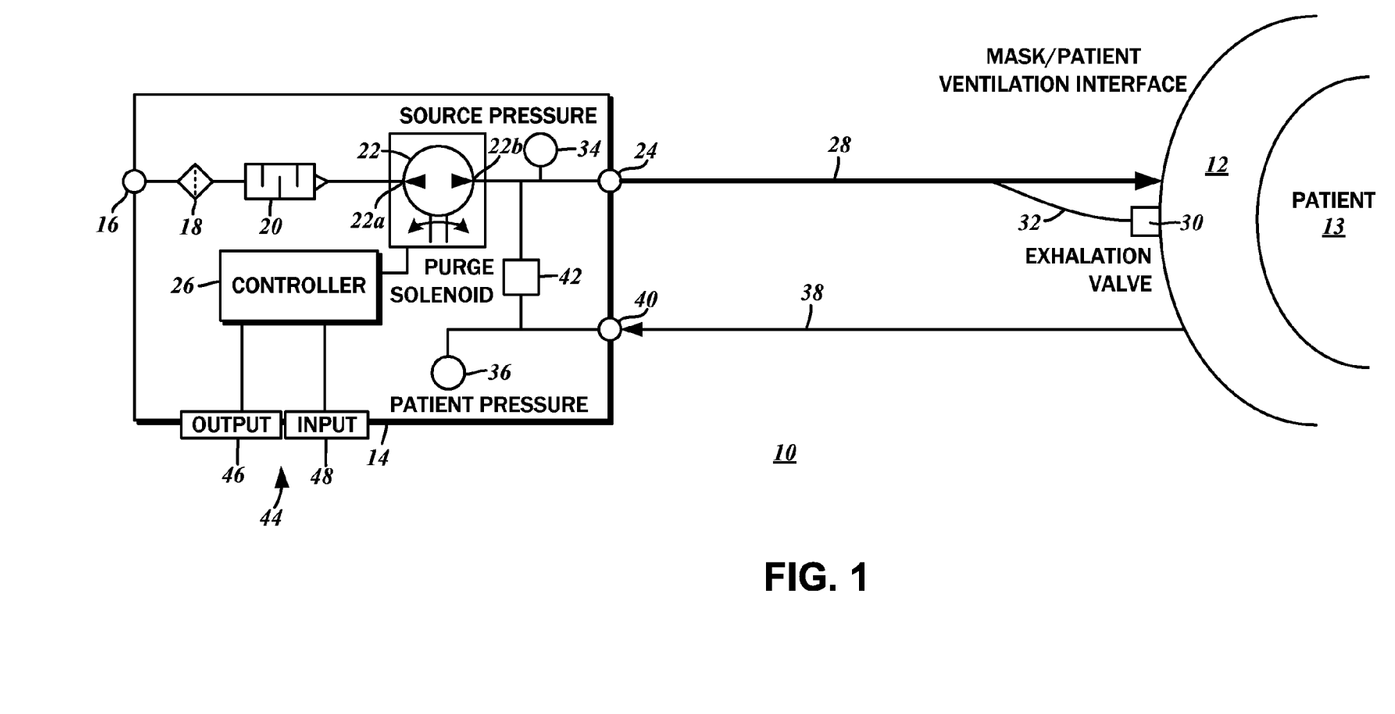
FIG. 1 is a block diagram showing the various components of a CPAP device in accordance with various embodiments of the present disclosure including a typical ventilation unit, a patient ventilation interface, and gas passage conduits.

The block diagram of FIG. 1 illustrates an exemplary respiratory assistance device 10 in which various embodiments of the present disclosure may be implemented. There is a mask or patient interface 12, and a ventilation unit 14. The following disclosure will make reference to the patient interface 12 and the mask interchangeably. It is understood to be an apparatus such as a full-face mask or a nasal pillows mask that can be placed in direct gas flow communication with the upper respiratory tract, i.e., the nasal cavity and/or the oral cavity, of a patient 13. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient interface 12. The breathing gas may be ambient air a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22, which may be a centrifugal fan, blower, or any other suitable device that generates gas flow and pressure suitable for CPAP treatment in accordance with the present disclosure. The ventilation source 22 has an inlet port 22a coupled to the sound suppressor 20, and an outlet port 22b that is in gas flow communication with an outlet port 24 of the ventilation unit 14. The ventilation source 22 is driven electrically and its actuation is governed by a controller 26, which implements various methods of CPAP treatment such as those disclosed in the co-pending U.S. patent application Ser. No. 13/411,257 entitled "DUAL PRESSURE SENSOR CONTINUOUS POSITIVE AIRWAY PRESSURE (CPAP) THERAPY," filed Mar. 2, 2012, the disclosure of which is hereby incorporated by reference in its entirety herein.

The flow of breathing gas that is output from the ventilation source 22 is passed through the outlet port 24 to a gas conduit 28 that is in coupled to the aforementioned patient interface 12. The gas conduit 28 is understood to be a plastic tube having a predetermined inner diameter such as 22 mm or smaller, though any other conduit of suitable material and construction may be utilized. The patient interface 12 in accordance with various embodiments of the present disclosure also includes a piloted valve 30 that is selectively actuated depending on the pressure differential between the patient interface 12 and the ventilation unit 14. The valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient interface 12, including the piloted valve 30 thereof, are presented by way of example only and not of limitation. Any other suitable patient interface 12, including those that may be utilized in conjunction with different variations of the ventilation unit 14, may be substituted without departing from the scope of the present disclosure.

In order to ascertain such pressure differentials, the presently contemplated respiratory assistance device 10 includes dual pressure sensors, including a source pressure sensor 34 and a patient interface sensor 36. The source pressure sensor 34 is disposed within the ventilation unit 14, and monitors the pressure at the outlet port 22b. The patient interface pressure sensor 36 is also physically disposed within the ventilation unit 14, but is in direct gas flow communication with the patient interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear the pressure sensor line 38. This can be done through a purge solenoid 42 connected to both. The purge can be continuous or intermittent according to the patient's breathing phase or pressure difference between the blower pressure and the mask pressure.

As indicated above, the sequence and timing of delivering gas flow to the patient 13 are governed by the specific treatment modalities that utilize feedback data from the pressure sensors 34, 36. The setting of options relating to the treatment modalities, along with the starting and stopping of treatment is possible via a user interface 44 coupled to the controller 26, which includes an output or display interface 46, as well as an input interface 48.

Figure 2:
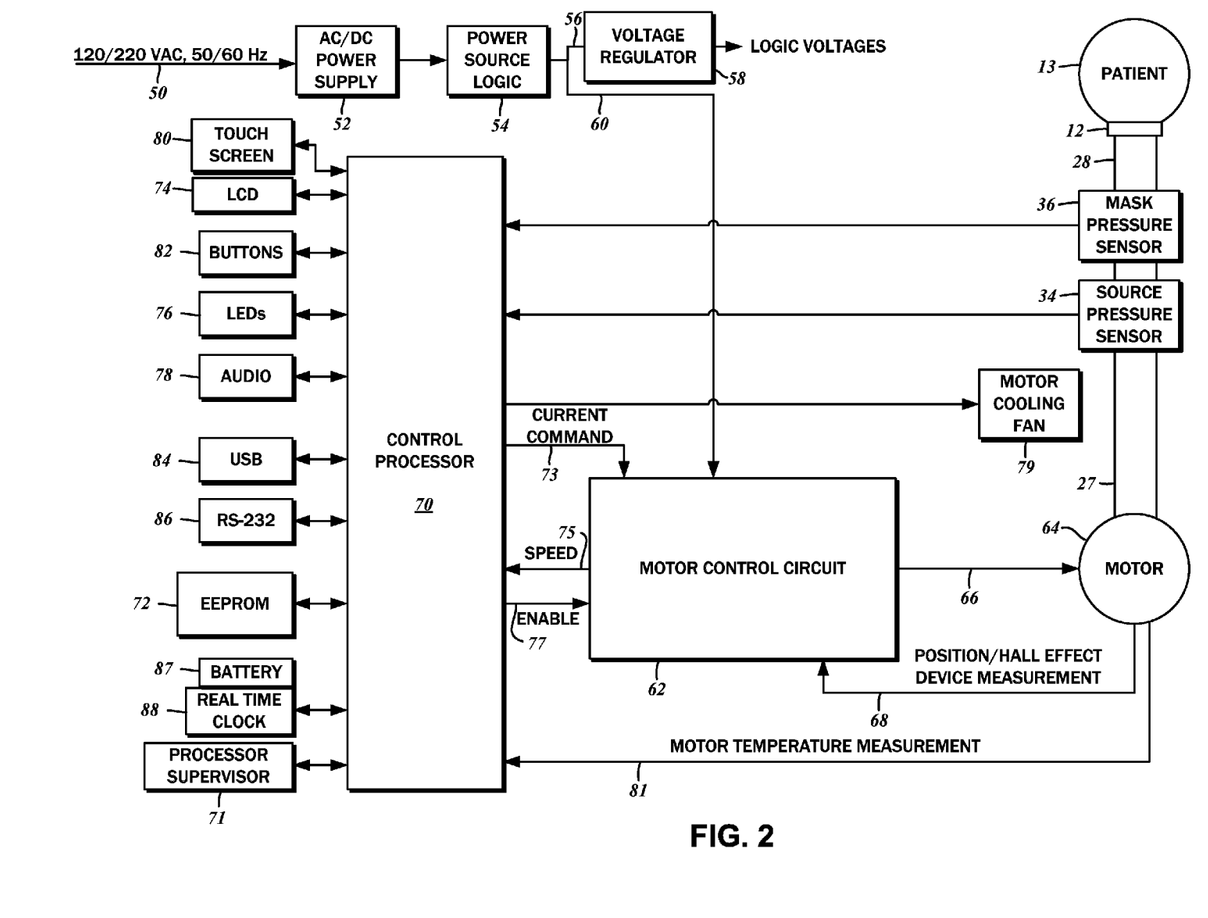
FIG. 2 is a block diagram illustrating the electrical components of the ventilation unit.

The block diagram of FIG. 2 illustrates the various electrical components of one typical embodiment of the ventilation unit 14. Power for the ventilation unit 14 may be provided from a conventional household electricity supply of either 120V or 220V alternating current (AC), at 50 Hz or 60 Hz. The block diagram denotes this supply as a power source 50. A power supply 52 is connected to the power source 50, and as will be recognized by those having ordinary skill in the art, the power signal is variously rectified, filtered, and stepped down to a direct current (DC) voltage. In accordance with one embodiment of the present disclosure, the DC voltage source is 24 V. It is understood that the ventilation source 22 utilizes a higher DC voltage than control logic devices, and thus the power supply 52 is connected to a power source logic 54. A first output 56 of the power source logic 54 is connected to an integrated circuit voltage regulator 58 that steps down the DC voltage to the logic device level of 5V. A second output 60 of the power source logic 54 is the existing high DC voltage directly from the power supply 52, and is connected to a motor control circuit 62.

The ventilation source 22 is comprised of several electrical components, including a motor 64 and the aforementioned motor control circuit 62. In accordance with one embodiment, the motor 64 is a brushless DC or electrically commutated motor. It will be recognized that the speed of rotation of the motor 64 is based upon input logic signals provided to the motor control circuit 62, which drives electrical current through its windings that induce magnetic fields that translate to rotational motion of the attached rotor. A fan coupled to the rotor thus rotates and generates a flow of air through an internal conduit 27. The internal conduit 27 is coupled to the outlet port 24, which is coupled to the gas conduit 28. As described above, the source pressure sensor 34 and the patient interface pressure sensor 36 are connected to the pneumatic circuit between the motor 64 and the patient 13.

The motor control circuit 62 has a motor drive output 66 that is connected to the motor 64. The rotational position of the motor 64 is detected by a Hall-effect sensor that is incorporated into the motor 64. An output voltage 68 from the Hall-effect sensor is fed back to the motor control circuit 62, which ensures that the actual position corresponds to the intended or commanded position.

The controller 26 and its functionality may be implemented with a programmable integrated circuit device such as a microcontroller or control processor 70. Broadly, the control processor 70 receives certain inputs, and based upon those inputs, generates certain outputs. The specific operations that are performed on the inputs may be programmed as instructions that are executed by the control processor 70. In this regard, the control processor 70 may include an arithmetic/logic unit (ALU), various registers, and input/output ports. Although external memory such as EEPROM (electrically erasable/programmable read only memory) 72 may be connected to the control processor 70 for permanent storage and retrieval of program instructions, there may also be an internal random access memory (RAM). One embodiment contemplates the use of an Intel 8081 instruction set/architecture, though any other suitable instruction set or processor architecture may be substituted. As indicated above, the control processor 70 is powered by a low voltage DC supply from the voltage regulator 58.

As mentioned above, in order to set the operational parameters of the ventilation unit, and to initiate or terminate certain functions, a graphical user interface is provided. Such graphical user interface is generated on a display screen 74, which may be of a liquid crystal type (LCD). Any type of graphic may be shown on the display screen 74, though for more specific indicators, a simple light emitting diode (LED) device 76 may be utilized. It will be recognized that alarm conditions, power status, and the like may be indicated with the LED device 76. Audible outputs may also be produced with audio transducers 78 that are likewise connected to the control processor 70. Among the contemplated outputs that may be generated on the audio transducer 78 include simple beeps and alarms, as well as sophisticated voice prompts that provide information and instructions.

An operator may interact with the graphical user interface through different input devices such as a touch screen interface 80 that is overlaid on the display screen 72. It will be recognized that various graphic elements may be generated on the display screen 72, with touch inputs/interactions corresponding in position to those graphic elements being evaluated as a selection or activation of the same. Various touch screen interfaces, some of which may be directly integrated with the display screen 72, are known in the art. Besides touch screen inputs, buttons 82 may also be connected to the control processor 70 for similarly receiving user inputs. It is understood that the audio transducer 78 may also accept sound input in the form of voice commands, the processing of which is performed may be performed by the control processor 70.

Several modalities for connecting to and communicating with other data processing devices such as general-purpose computers are also contemplated. Accordingly, the control processor 70 may be connected to a universal serial bus (USB) controller 84. For more basic communications, there may be a serial RS-232 transceiver 86. Through these data communications modalities, the configuration options of the ventilation unit 14 may be set, operating profiles may be downloaded, and so forth. Notwithstanding the specific reference to USB and RS-232 communications modalities, any other communications modality including wireless systems may be substituted without departing from the present disclosure.

The functions of the ventilation unit 14 depend on proper synchronization, and so the control processor 70 is connected to a real time clock 88 that maintains a common clock cycle. Although a primary feature of the real time clock 88 is to maintain synchrony at a processor cycle level, longer term time data is also maintained. In order to retain such time data, the real time clock 88 may be powered independently of the primary power source 50, and there is accordingly a battery backup 87. Under heavy processing loads or unexpected program conditions, the control processor 70 may become unable to execute critical programmed steps in real-time. Thus, the control processor 70 may include a processor supervisor 71 that invokes a program execution break upon detecting such conditions. Typically, this is implemented as a step of clearing a memory variable periodically, and when that step is unable to take place because instruction execution is frozen or otherwise delayed, the processor supervisor 71 may cause a predetermined routine to be executed.

As mentioned above, the motor 64 is driven by the motor control circuit 62, which generates different outputs depending on signals received from the control processor 70. The signal to drive the motor 64 is generated on a current command line 73. For control processing on a broader level, feedback from the ventilation source 22 is utilized, and in the specific form of a speed or current measurement input 75 from the motor control circuit 62. Furthermore, as detailed below, pressure readings at the ventilation source 22 and the patient 13 are utilized to reach control decisions. Accordingly, the source pressure sensor 34 and the patient interface pressure sensor 36 are both connected to the control processor 70. The ventilation source 22 is activated and deactivated via a motor enable line 77. To ensure that the temperature of the motor 64 remains within operational parameters, a motor cooling fan 79 may be driven directly by the control processor 70. In some embodiments, there may be additional control circuitry that isolates the power source of the motor cooling fan 79 from the control processor 70. The decision to activate and deactivate the motor cooling fan 79 may be made in response to temperature readings from the motor 64, and so there is a motor temperature reading 81 passed to the control processor 70.

Notwithstanding the foregoing description of the particular respiratory assistance device 10, the contemplated method of operation and a system configured for such operation can be adapted to any other respiratory assistance device 10. The present disclosure contemplates adapting the output pressure of therapeutic gas to patient breathing. This may be based on measuring comfort, in particular, the pressure at the patient airway, for example, the nose in the case of a patient interface 12 that is nasal mask, as a representation of such comfort. From the pressure measurement at the patient airway, a comfortable and suitable pressure maneuver may be provided, so that the patient can be more comfortable as feeling more in synchronization with his or her spontaneous breathing.

Figure 3:
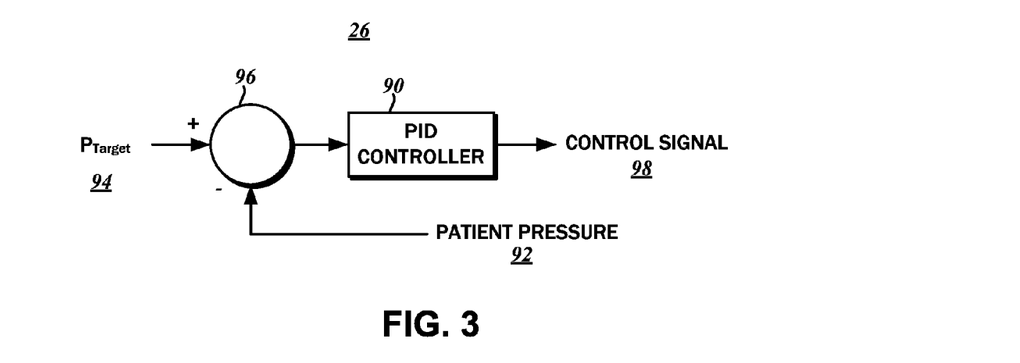
FIG. 3 is a generalized control diagram of the CPAP device according to one embodiment of the present disclosure in which a control signal corresponding to a comfort signature is generated by a proportional, integral, derivative controller with patient pressure and a target pressure as inputs.

The system is based on a direct pressure measurement at the patient airway. In one exemplary embodiment shown in FIG. 3, a proportional, integral, derivative (PID) controller 90 receives an input of patient pressure values 92 from the patient interface sensor 36, along with a target pressure value 94. These two values are evaluated at a summing point 96 and provided to the PID controller 90. Based upon the difference between the target pressure value 94 and the patient pressure value 92 as evaluated by the PID controller 90, appropriate adjustments are made to the output control signal 98. Those having ordinary skill in the art will recognize the operation of the PID controller 90 to output corrective signals that more closely bring the patient pressure value 92 to the target pressure value 94, and will not be repeated herein. In a conventional CPAP system, the target pressure is a constant value.

Figure 4:
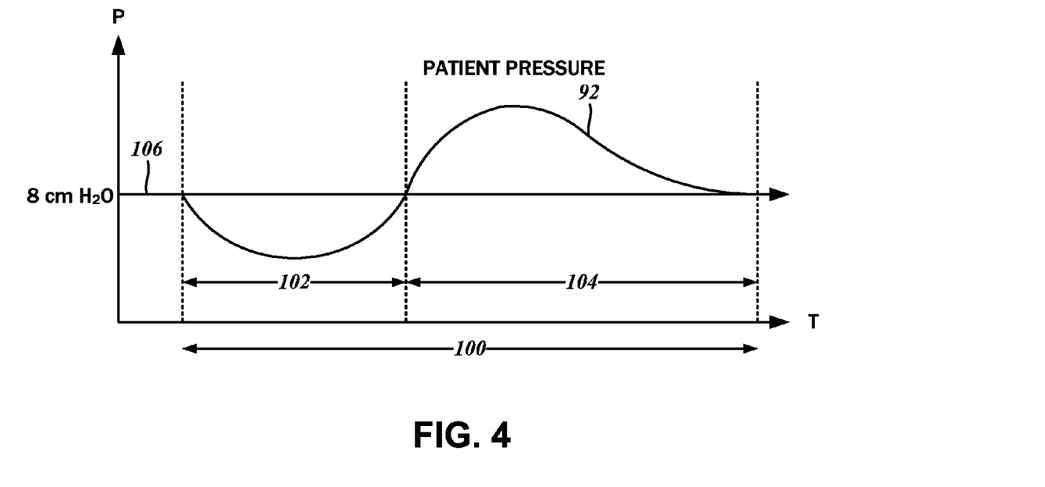
FIG. 4 is a graph of patient airway pressure in a conventional CPAP system superimposed over a constant target pressure signal.

The graph of FIG. 4 shows an exemplary plot of measurements of pressure at the patient 13. This plot of the patient pressure value 92 is over a single respiration cycle 100 characterized by an inspiratory phase 102 and an expiratory phase 104 that follows the inspiratory phase. There is additionally shown a plot 106 of a constant pressure output, e.g., 8 cm H2O as generated by the ventilation source 22. During the inspiratory phase 102, the pressure at the patient 13 drops below the constant pressure output, while during the expiratory phase 104, the pressure rises above the constant pressure output. This increased pressure is understood to be felt as a sensation of asphyxiation and increased resistance to spontaneous breathing by the patient 13.

With reference to the graph of FIG. 4, the operation of one embodiment of the comfort signature pressure adjustments will be described. Generally, the signal of the target pressure 94 is adjusted and shaped in real time, which serves as the basis for adjusting the output control signal 98 from the PID controller, with comparisons to the actual patient pressure 92. In all other respects, the pressure controller 26 does not function differently from a conventional, constant target pressure delivery CPAP implementation.

Figure 5:
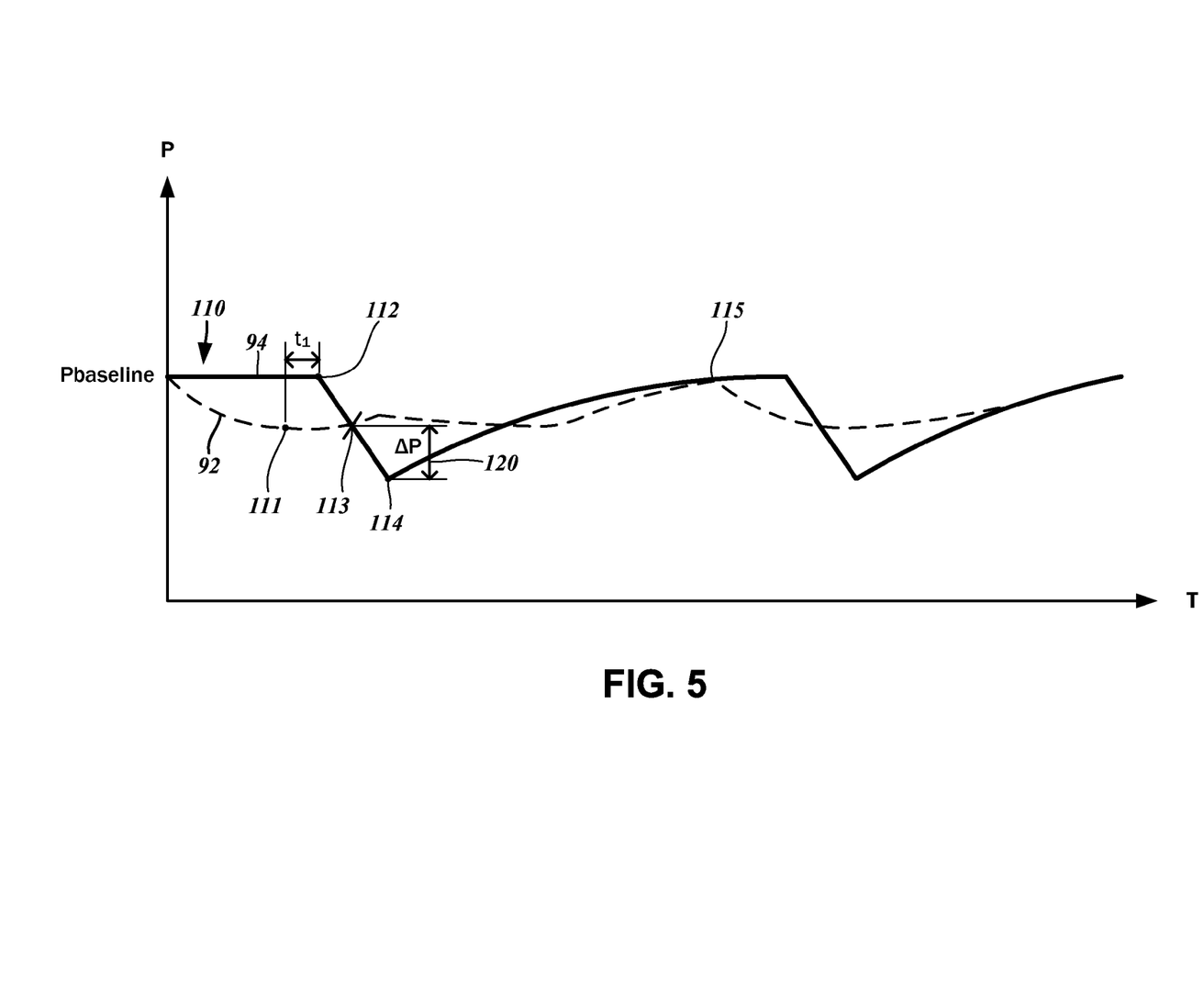
FIG. 5 is a graph of patient airway pressure in the CPAP device that utilizes a comfort signature superimposed over a signature value signal.

The graph of FIG. 5 shows a plot 110 corresponding to the target pressure 94 as shaped by the comfort signature. Additionally, there is a plot of the measured patient pressure 92, which depicts an exemplary ideal response to the variable target pressure. First, with the target pressure set at the prescription level, the minimum value of the patient pressure 92 is detected. This is understood to correspond to the time of onset of expiration at a first time instant 111. After a predefined time t1 after the detected onset of expiration, the target pressure 94 is linearly reduced starting from a second time instant 112. Although a linear reduction is shown, those having ordinary skill in the art will recognize that any other mathematical function may be substituted without departing from the scope of the present disclosure.

The reduction in the target pressure 94 continues past the contemporaneously measured patient pressure 92 at a third time instant 113, until a predetermined pressure difference 120 is detected at a fourth time instant 114. This time period may also be referred to as the comfort zone, and represents an area of minimal resistance to spontaneous breathing resulting from the splinting prescription pressure. The pressure difference 120 may be set by the user and/or medical practitioner. Thereafter, the target pressure 94 is increased to the prescription level until a fifth time instant 115, at which point the patient begins expiring again.

During exhalation with a conventional constant target pressure system, pressure tends to go above the target pressure, resulting in the feeling of asphyxiation and also of increased resistance. Utilizing the present system, however, pressure relief may be started earlier than other techniques because initiation of pressure decrease occurs at the onset of exhalation and not at the beginning of exhalation. Additionally, the reduction of pressure below the level of the patient's pressure allows for adaptation of the signature value signal to each breath individually.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:

1. A method for adjusting continuous positive airway pressure (CPAP) therapy for patient comfort on a respiratory assistance device, the method comprising:
   setting a target delivery pressure to a prescription pressure level;
   generating by a ventilation source on the respiratory assistance device an output of therapeutic gas to an airway of the patient in pneumatic communication therewith over a patient interface, pressure of the output corresponding to the target delivery pressure as set to the prescription pressure level;
   receiving on the respiratory assistance device patient pressure values measured at the patient interface by a pressure sensor;
   detecting a minimum value among the received patient pressure values over a first predetermined time period; and
   reducing by a controller the target delivery pressure following a predefined delay after detecting the minimum value of the received patient pressure values until the target delivery pressure is below a contemporaneously measured patient pressure value.

2. The method of claim 1, further comprising:
   increasing the target delivery pressure to the prescription level in response to the target delivery pressure being evaluated as below the contemporaneously measured patient pressure value.

3. The method of claim 1, wherein the target delivery pressure is reduced until a difference between the target delivery pressure and the contemporaneously measured patient pressure value reaches a predefined threshold.

4. The method of claim 3, further comprising:
   increasing the target delivery pressure to the prescription level in response to the difference between the target delivery pressure and the contemporaneously measured patient pressure value reaching the predefined threshold.

5. The method of claim 3, further comprising:
   receiving on the respiratory assistance device a value of the predefined threshold for the difference between the target delivery pressure and the contemporaneously measured patient pressure value.

6. The method of claim 1, further comprising:
   receiving on the respiratory assistance device a value of the prescription pressure level.

7. The method of claim 1, further comprising:
   receiving on the respiratory assistance device a value of the predefined delay.

8. The method of claim 1, wherein the target delivery pressure is reduced linearly.

9. The method of claim 1, wherein the first predetermined time period is within a patient inspiratory phase in a spontaneous respiration cycle of the patient.

10. The method of claim 1, wherein the detection of the minimum value among the received patient pressure values over the first predefined time period corresponds to an onset of a patient expiratory phase in a spontaneous respiration cycle of the patient.

11. The method of claim 1, further comprising:
    generating on the respiratory assistance device the output of therapeutic gas to the airway of the patient, pressure of the output being reduced according to the reduction of the target delivery pressure following the predefined delay after detecting the minimum value of the received patient pressure values.

12. A method for adjusting target delivery pressure to a patient undergoing continuous positive airway pressure therapy, the method comprising:
    detecting by a controller a minimum value of patient pressure, measured by a pressure sensor, corresponding to a time of onset of patient expiration;
    reducing by the controller target pressure following a variable time after the detecting of the minimum value of patient pressure, until actual delivered pressure is evaluated by the controller as being at least below the target pressure; and
    increasing the target pressure after and in response to the actual delivered pressure is evaluated as being at least below the target pressure.

13. The method of claim 12, wherein the target pressure is reduced until the actual delivered pressure has a preset pressure difference with the target pressure.

14. The method of claim 13, wherein the target pressure is increased after the actual delivered pressure has the preset pressure difference with the target pressure.

15. The method of claim 13, wherein the preset pressure difference is user-defined.

16. The method of claim 12, wherein the target pressure is reduced linearly.

17. The method of claim 12, wherein the target pressure is increased to a prescription level.

* * * * *